United States Patent [19]

Stoffey et al.

[11] 4,068,082

[45] Jan. 10, 1978

[54] PROCESS FOR PREPARING ESTERS

[75] Inventors: Donald G. Stoffey, Hacienda Heights; Jan Alexander Orlowski, Altadena, both of Calif.

[73] Assignee: Lee Pharmaceuticals, South El Monte, Calif.

[21] Appl. No.: 398,877

[22] Filed: Sept. 19, 1973

Related U.S. Application Data

[63] Continuation of Ser. No. 120,340, March 2, 1971, abandoned.

[51] Int. Cl.$^2$ .................... C07C 67/14; C07C 69/54; C07C 69/80; C07C 69/82
[52] U.S. Cl. ........................ 560/90; 560/85; 560/86; 560/89; 560/95; 560/98; 560/107; 560/108; 560/112; 560/113; 560/198; 560/199; 560/201; 560/204; 560/205; 560/221; 560/224; 560/225; 560/240; 560/261; 560/263; 560/265
[58] Field of Search .......... 260/475 N, 476 R, 485 N, 260/479 R, 486 R, 496, 488 H, 488 J, 488 F, 485 G, 485 R, 475 P, 475 PN

[56] References Cited

U.S. PATENT DOCUMENTS

| | | | |
|---|---|---|---|
| 3,539,526 | 11/1970 | Bowen | 260/475 P |
| 3,629,197 | 12/1971 | Stiehl | 260/486 R |

FOREIGN PATENT DOCUMENTS

| | | | |
|---|---|---|---|
| 1,204,970 | 9/1970 | United Kingdom | 260/479 R |
| 1,191,270 | 5/1970 | United Kingdom | 260/476 R |

OTHER PUBLICATIONS

Fieser et al., Reagents for Organic Synthesis, p. 1110, (1967).

*Primary Examiner*—Jane S. Myers
*Attorney, Agent, or Firm*—Irons and Sears

[57] ABSTRACT

Esters are prepared by reaction of acyl halides and alcohols or hydroxyalkyl esters and acid halides in the presence of a tertiary amine and polar aprotonic solvents. Bis(2-methacrylatoethyl) phthalate is prepared by the reaction of phthaloyl chloride with 2-hydroxyethyl methacrylate in pyridine and acetone. Bisphenol-A-bis(2-methacrylatoethyl)ether is prepared from 2,2-bis[4-(2-hydroxyethoxy)phenyl]-propane and methacryl chloride in acetone.

2 Claims, No Drawings

PROCESS FOR PREPARING ESTERS

BENEFIT OF PRIOR APPLICATION

This application is a continuation of application Ser. No. 120,340, filed Mar. 2, 1971, now abandoned.

BACKGROUND OF THE INVENTION

1. Field of the Invention

This invention is concerned with an improved process for the preparation of esters by the reaction of acyl halides and alcohols or by the reaction of hydroxyalkyl esters with acid halides of acids wherein the reactions are carried out in the presence of a tertiary amine as an acceptor for the hydrogen halide generated in the reaction. The invention is especially concerned with an improved process of this type for the preparation of bis-acrylates from an acryl chloride and a diol, or a hydroxyalkyl acrylate and a dicarboxylic acid chloride.

2. Description of the Prior Art

In the past, many esters have routinely been prepared by the reaction of an acyl halide and an alcohol in a non-polar solvent such as toluene or chloroform using a tertiary amine as an acceptor for the hydrogen halide generated in the reaction. Such esters have also been prepared by the reaction of hydroxyalkyl esters with acid halides of carboxylic acids. By way of exemplification, bisacrylates have usually been prepared by the reaction of an acryl chloride and a diol in a non-polar solvent using a tertiary amine such as triethylamine as an acceptor for the hydrogen chloride generated in the reaction. In a similar manner bisacrylates have also been prepared by the reaction of hydroxyalkyl acrylates with acid chlorides of dicarboxylic acids. While these reactions have been routinely carried out in non-polar solvents using tertiary amines as acceptors for the hydrogen halide generated in the reaction, a number of drawbacks are presented, however, when it is attempted to recover the end products from the reaction mixture. In order to remove the amine hydrohalide which is formed, the reaction mixture in the past has been washed with water, and then treated with dilute acid to remove excess amine. It has often happened in the past that with the addition of the water or the dilute acid, emulsions were formed which were very hard to break. In many instances, the desired products were degraded by hydrolysis or undesired polymerization occurred before the emulsion could be broken.

Examples of compounds which have been prepared by these reactions in the past are monomeric bisacrylic resins such as the following:

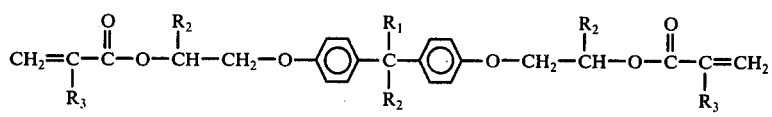

wherein $R_1$, $R_2$ and $R_3$ are either hydrogen or lower alkyl groups preferably comprising 4 or less carbon atoms, especially the compounds bis-phenol-A-bis(2-methacrylatoethyl) ether which is represented by the formula:

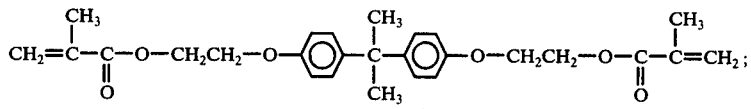

bisphenol-F-bis(2-methacrylatopropyl) ether which is represented by the following formula:

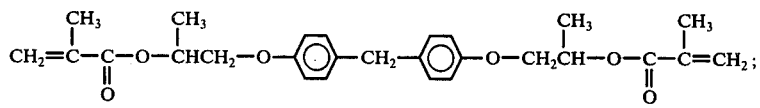

bis(2-methacrylatoethyl) phthalate which is represented by the following formula:

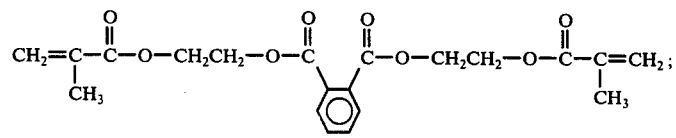

bis(2-methacrylatoethyl) isophthalate which is represented by the following formula:

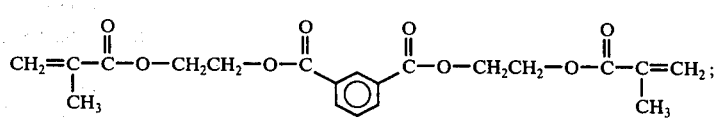

bis(2-methacrylatoethyl) terephthalate which is represented by the following formula:

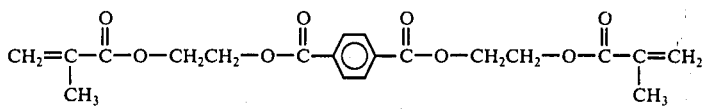

and the bismethacrylate ester of bisphenol-A which is represented by the following formula:

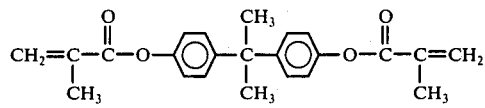

The foregoing monomer compounds may be polymerized to form useful coatings and other protective finishes. They have also been found useful in dental restorative compositions when blended with inorganic fillers.

While it is known to prepare esters by the relatively simple reactions outlined above, for example, in the case of bisacrylates by the reaction of the acryl chloride with a diol or a hydroxyalkyl acrylate and the acid chloride of a dicarboxylic acid, in each instance, in the presence of a tertiary amine serving as an acceptor for the hydrogen chloride generated, the recovery of the end products from the reaction mixtures of these reactions has suffered from deficiencies caused by the formation of relatively stable emulsions when the reaction mixture was washed with water in order to remove the amine hydrochloride or washed with dilute acid to remove excess amine. The emulsions formed were generally hard to break and made recovery of the desired end product difficult. For example, in the case of the acrylate type of products, they were often partially degraded by hydrolysis or undesired polymerization occurred before the emulsion could be broken.

SUMMARY OF THE INVENTION

The purpose of the present invention is to provide an improved process of making ester compounds. Esters which are prepared by the process of this invention previously have been prepared by the reaction of an acyl halide and an appropriate alcohol or by the reaction of a hydroxyalkyl ester and an acid halide in the presence of tertiary amines as acceptors for the hydrogen halide generated during the reaction. The ester compounds are insoluble in the water-solvent system utilized. As indicated in the previous processes, the reactions were carried out in non-polar solvents such as toluene or chloroform.

It has been discovered that these processes may significantly be improved by conducting the reaction in a polar-aprotonic solvent as the reaction medium. By employing polar-aprotonic solvents as the reaction medium, the formation of emulsions when the reaction mixture is washed with water to remove the amine hydrohalide or upon washing with dilute acid to remove excess amine, is eliminated. With the elimination of the formation of the unwanted emulsions which are difficult to break, degradation of the end products by hydrolysis or unwanted polymerization is eliminated. Besides eliminating the undesired reactions, the process of the present invention is faster and easier than the previous method.

DESCRIPTION OF THE PREFERRED EMBODIMENTS

As mentioned above, the process of making ester compounds by the reaction of an acyl halide and an appropriate alcohol and by the reaction of a hydroxyalkyl ester with an acid halide of a carboxylic acid in the presence of a tertiary amine as an acceptor for the hydrogen halide generated is greatly improved by carrying out the reaction in a polar-aprotonic solvent. The esters produced according to the improved process of the present invention must be insoluble in the water/polar aprotonic solvent system utilized in recovery of the ester product. The type of reactions to which the improvement of the present invention is applicable is illustrated in the following schematic diagram:

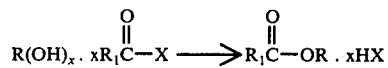

wherein R and $R_1$ are alkyl, substituted alkyl, alkenyl, substituted alkenyl, aryl, or substituted aryl, X is a halide, preferably chlorine, and $x$ is a positive integer, preferably 1 or 2.

Representative preferred embodiments of the invention are illustrated by the following:

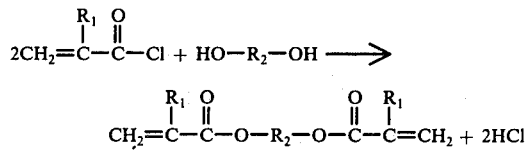

wherein $R_1$ is hydrogen or lower alkyl preferably methyl, and $R_2$ is the appropriate divalent radical derived from the diol, and

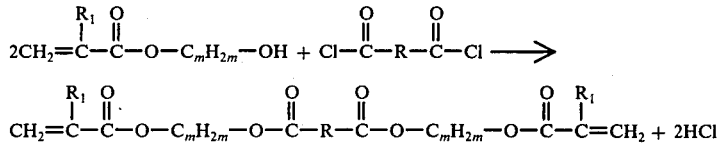

wherein $R_1$ is as defined above, R is a radical derived from the appropriate dicarboxylic acid and $m$ is an integer of 2 to 4.

The term -ol- in this specification includes both alcoholic and phenolic hydroxyl groups. Thus, diol includes both aliphatic and aromatic dihydroxy compounds.

Since in the present invention a dry polar-aprotonic solvent such as, for example, acetone or tetrahydrofuran is used as the reaction medium, and these solvents are miscible with water, the reaction may be subsequently worked up by pouring the reaction mixture into water. The amine hydrochloride and solvent dissolve in the water and the product is isolated as a solid, or as an oil as the case may be.

If the end product is a solid, the addition of ice into the water will help solidify the product. In general, the temperature of the water-ice system is lowered to about $-10°$ C to $-20°$ C. In case of a solid product, it can be isolated by filtration and washed with water to remove most of the solvent and amine salt. Thereafter the solid product is purified by usual recrystallization techniques. In the majority of cases, since methanol is the most preferred recrystallization solvent, the crude product need not be dried since the water will be removed by the methanol solvent.

The following examples describing certain specific embodiments of the invention will serve to further illustrate the nature of the invention.

EXAMPLE 1

Bis(2-methacrylatoethyl) phthalate 203 g. of phthaloyl chloride is added slowly to a mixture of 273 g. of 2-hydroxyethyl methacrylate, 190 g. of pyridine and 200 ml. of dry acetone. The temperature of the mixture is maintained below 15° C during mixing. After the addition of the phthaloyl chloride, the reaction temperature is allowed to rise to 25° C, and, thereafter, the reaction mixture is poured into a 250 ml. mixture of water and ice. A small amount of dry ice and a few seed crystals are added to the system to accelerate the solidification of the product. The solid is filtered and washed with 200 ml. of cold water. The crude product is recrystallized from 400 ml. of methanol to a yield upon drying of 245 g. (63% yield) of a white solid having a melting point of 40°–42° C.

EXAMPLE 2

Bis(2-methacrylatoethyl) terephthalate

The procedure of EXAMPLE 1 is repeated but employing in place of the phthaloyl chloride, terephthaloyl chloride. The bis(2-methacrylatoethyl) terephthalate obtained has a melting point of 49°–50.5° C.

EXAMPLE 3

Bis(2-methacrylatoethyl) isophthalate

The procedure of EXAMPLE 1 is repeated but employing in place of the phthaloyl chloride, isophthaloyl chloride. The bis(2-methacrylatoethyl) isophthalate obtained has a melting point of 40.5°–41.5° C.

EXAMPLE 4

Bis-phenol-A-bis(2-methacrylatoethyl) ether 45 g. of methacryl chloride is slowly added to a mixture of 66.2 g. of 2,2-bis[4-(2-hydroxyethoxy)phenyl]-propane, 41 g. of triethylamine and 300 ml. of dry acetone. The temperature is maintained below 32° C with cooling. The resulting amine hydrochloride is filtered off and washed with acetone. The acetone solution is added to 500 ml. of ice and water, the oily layer recovered and washed with sodium bicarbonate, followed by water, and dried at 40° C. in a vacuum with a stream of air passing through the liquid. The infrared spectrum of the product contains only a very small band indicating hydroxyl hydrogens, a large ester carbonyl band, and a carbon double bond band.

EXAMPLE 5

Bis-phenol-F-bis(2-methacrylatopropyl) ether

Following the same general procedure utilized in EXAMPLE 4, bis-phenol-F-bis(2-methacrylatopropyl) ether is prepared by the reaction of bis[4-(2-hydroxypropoxy)phenyl] methane and methacryl chloride.

EXAMPLE 6

Bismethacrylate ester of Bisphenol-A

The procedure of EXAMPLE 4 is followed in preparing bismethacrylate ester of bisphenol-A by the reaction of bisphenol-A with methacryl chloride. The desired product is recrystallized from methanol to give an 85% yield of a white crystalline ester. The melting point is 74°–75.5° C.

EXAMPLE 7

Commercial hydrogenated bisphenol-A obtained from Monsanto Chemical Company is a glassy solid separated into two fractions by treatment with benzene. One fraction which begins to melt at 50° C dissolves easily in the usual solvents. The second, and more insoluble fraction, melts at 120°–175° C. The commercial product which is obtained melts from 50° to 120° C.

a. To a mixture of 60 g. of the high melting hydrogenated bisphenol-A, 60 g. of triethylamine and 400 ml. of tetrahydrofuran, there is slowly added 54 g. of methacryl chloride, the temperature being maintained at 35° C. The addition with stirring takes 90 minutes. Following the addition of the methacryl chloride, the amine salt is filtered off and the filtrate added to 800 ml. of ice and water. The mixture is stored at $-22°$ C for 16 hours. The solid product is filtered off, washed with heptane and dried in an oven at 60° C. The infrared spectrum shows only a small amount of hydroxy group.

b. To a mixture of 100 g. of the lower melting hydrogenated bis-phenol-A, 100 g. triethylamine and 60 ml. of dry acetone, maintained at 30° C, there is slowly added 88 g. of methacryl chloride. The temperature is maintained between 25°–30° C. Following the addition of the methacryl chloride, the amine salt formed is filtered off and the filtrate added to 2 litres of ice and water. The lower, oil layer which formed is separated and dried over anhydrous magnesium sulfate. A trace of hydroquinone is added to prevent polymerization. The remaining solvent is removed in a rotary evaporator to yield a pale amber viscous oil. The infrared spectrum indicates the presence of ester and vinyl groups.

We claim:

1. In a process for making esters of the formula

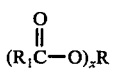

by the reaction of a compound of the formula

with a compound of the formula

wherein R and $R_1$ are each independently alkyl, substituted alkyl, alkenyl, substituted alkenyl, aryl, or substituted aryl, and X is halogen, and x is a positive integer, in the presence of sufficient tertiary amine as an acceptor for the hydrogen halide generated by the reaction, the improvement which comprises conducting said reaction in a polar aprotonic solvent as the reaction medium, wherein the solvent is comprised of acetone.

2. In a process for making bis acrylates by the reaction of an acryl halide with a diol, or by the reaction of a hydroxyalkyl acrylate with a dicarboxylic acid halide, in the presence of sufficient tertiary amine as an acceptor for the hydrogen halide generated by the reaction, the improvement which comprises conducting said reaction in acetone as the reaction medium.

* * * * *